United States Patent
Sheng et al.

(10) Patent No.: US 11,117,875 B2
(45) Date of Patent: Sep. 14, 2021

(54) CRYSTALLINE FORMS, PREPARATION METHODS AND PHARMACEUTICAL COMPOSITIONS OF OZANIMOD

(71) Applicant: Hangzhou SoliPharma Co., Ltd., Zhejiang (CN)

(72) Inventors: Xiaohong Sheng, Zhejiang (CN); Xiaoxia Sheng, Zhejiang (CN); Jianfeng Zheng, Zhejiang (CN)

(73) Assignee: Hangzhou Solipharma Co., Ltd., Zhejiang (CN)

( * ) Notice: Subject to any disclaimer, the term of this patent is extended or adjusted under 35 U.S.C. 154(b) by 0 days.

(21) Appl. No.: 16/333,287

(22) PCT Filed: Sep. 14, 2016

(86) PCT No.: PCT/CN2016/099137
§ 371 (c)(1),
(2) Date: Mar. 14, 2019

(87) PCT Pub. No.: WO2018/049632
PCT Pub. Date: Mar. 22, 2018

(65) Prior Publication Data
US 2019/0241530 A1    Aug. 8, 2019

(51) Int. Cl.
| | | |
|---|---|---|
| A61K 47/02 | (2006.01) | |
| A61K 47/10 | (2017.01) | |
| A61K 47/16 | (2006.01) | |
| A61K 47/08 | (2006.01) | |
| A61K 31/4245 | (2006.01) | |
| A61K 9/08 | (2006.01) | |
| A61K 9/19 | (2006.01) | |
| A61P 37/06 | (2006.01) | |
| A61P 11/00 | (2006.01) | |
| A61P 1/00 | (2006.01) | |
| A61P 19/02 | (2006.01) | |
| A61P 25/28 | (2006.01) | |
| C07D 271/06 | (2006.01) | |

(52) U.S. Cl.
CPC ............. *C07D 271/06* (2013.01); *A61K 9/08* (2013.01); *A61K 31/4245* (2013.01); *A61K 47/08* (2013.01); *A61K 47/10* (2013.01); *A61K 47/16* (2013.01); *A61P 1/00* (2018.01); *A61P 11/00* (2018.01); *A61P 19/02* (2018.01); *A61P 25/28* (2018.01); *A61P 37/06* (2018.01); *C07B 2200/13* (2013.01)

(58) Field of Classification Search
CPC ........ A61K 47/01; A61K 47/10; A61K 47/16; A61K 47/08; A61K 31/4245; A61K 9/08; A61K 9/19; A61P 37/06; A61P 25/28; A61P 1/00; A61P 11/00; A61P 19/02; C07D 271/06
See application file for complete search history.

(56) References Cited

U.S. PATENT DOCUMENTS 9,388,147 B2    7/2016 Martinborough et al.

FOREIGN PATENT DOCUMENTS

| CN | 102118972 B | 6/2015 | |
|---|---|---|---|
| WO | WO 2011/060392 A1 | 5/2011 | |
| WO | WO-2018033149 A1 * | 2/2018 | ................ A61P 1/00 |

OTHER PUBLICATIONS

WO2018033149-machine-translation, 2020, machine translation.*
Park et al., Biomol Ther, 25(1), 80-90, 2017.*
Mohammed et al., 2017, Frontiers in Immunology, vol. 8, p. 1-8.*
Ozanimod, 2021, https://en.wikipedia.org/wiki/Ozanimod.*
Zhi; J., et al., "Research and Development of Sphingosine 1-Phosphate Modulators," Progress in Pharmaceutical Sciences 40(7):548-54, China Pharmaceutical University (2016).
International search report for United States Application No. PCT/CN2016/099137, State Intellectual Property Office of the P.R. China, China, dated Jun. 19, 2017.

* cited by examiner

*Primary Examiner* — Sun Jae Yoo
(74) *Attorney, Agent, or Firm* — Sterne, Kessler, Goldstein & Fox P.L.L.C.

(57) ABSTRACT

The present invention relates to novel crystal forms of ozanimod. Compared with the prior art, the crystal forms of the present invention have one or more improved properties. The present invention also relates to preparation methods of the crystal forms, pharmaceutical compositions thereof and uses thereof for the manufacture of medicament for treating and/or preventing diseases or adverse conditions associated with modulation, activation, stimulation, inhibition or antagonization of selective sphingosine-1-phosphate (S1P) receptor.

17 Claims, 8 Drawing Sheets

CRYSTALLINE FORMS, PREPARATION METHODS AND PHARMACEUTICAL COMPOSITIONS OF OZANIMOD

FIELD OF THE INVENTION

The present invention relates to the technical field of crystallization in pharmaceutical chemistry. Specifically, the present invention relates to novel crystals, preparation methods and pharmaceutical compositions of ozanimod.

BACKGROUND

Ozanimod is a selective sphingosine-1-phosphate (S1P) receptor modulator, used for treatment for autoimmune diseases. Ozanimod shows strong data in pharmacokinetic, pharmacodynamic and safety in clinical trials, suitable for differentiated drug development strategies.

Ozanimod, also named RPC1063, has the chemical name of 5-[3-[(1S)-2,3-dihydro-1-(2-hydroxyethylamino)-1H-inden-4-yl]-1,2,4-oxadiazol-5-yl]-2-isopropoxybenzonitrile, molecular formula of $C_{23}H_{24}N_4O_3$, molecular weight of 404.46, and CAS number of 1306760-87-1. The chemical structure is shown in the following formula (I).

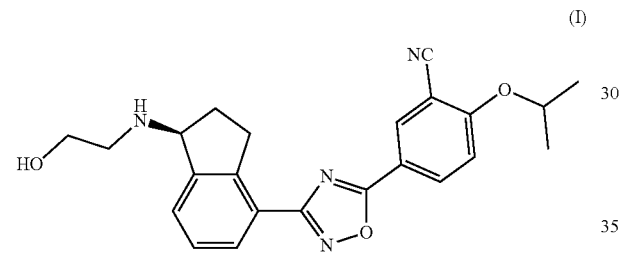
(I)

Patent CN102118972B and CN102762100B disclosed ozanimod, its preparation method and pharmaceutical compositions.

The present inventor finds that the ozanimod prepared according to CN102118972B has low crystallinity and poor stability.

In view of the disadvantages in the prior art, it is necessary to develop new solid forms of ozanimod with more advantageous properties.

SUMMARY OF THE INVENTION

The objective of the present invention is to provide novel crystals, preparation methods, pharmaceutical compositions and uses thereof of ozanimod. Compared with the known ozanimod in the prior art, the novel crystals in the present invention have one or more advantageous properties, especially its high crystallinity and good stability.

Comparing to the known solid forms of ozanimod in the prior art, the solid forms in the present invention have at least one or more advantageous properties, such as higher crystallinity, better solubility, faster dissolution rate, lower hygroscopicity, better storage stability, better flowability and processing characteristics. Preferably, the solid forms of the present invention have better crystallinity and stability.

According to an objective of the present invention, the present invention provides ozanimod Form 1 (herein after referred to as "Form 1"):

Form 1 is anhydrous, and its chemical structure is shown in the following Formula.

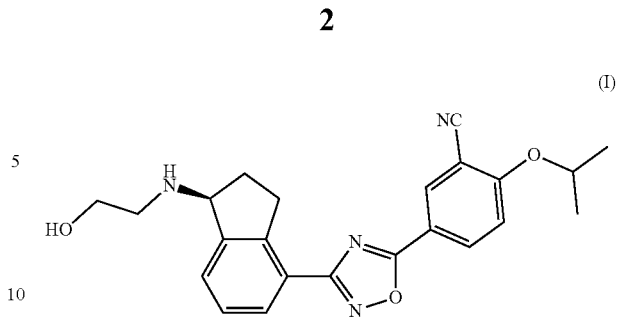
(I)

Using Cu-Kα radiation, the X-ray powder diffraction pattern of Form 1, expressed as 2θ angles, has the following characteristic peaks: 5.7±0.2°, 8.6±0.2°, 11.5±0.2°, 13.3±0.2°, 16.2±0.2° and 19.5±0.2°.

More preferably, the X-ray powder diffraction pattern of Form 1, expressed as 2θ angles, has the following characteristic peaks: 5.7±0.2°, 8.6±0.2°, 11.5±0.2°, 13.3±0.2°, 13.9±20.2°, 14.5±0.2°, 16.2±0.2°, 24.6±0.2°, 25.3±0.2°, 26.1±0.2° and 26.9±0.2°.

Further preferably, the X-ray powder diffraction pattern of Form 1, expressed as 2θ angles, has the following characteristic peaks with their relative intensities:

| Diffraction angel 2θ | Relative intensity % |
|---|---|
| 5.7 ± 0.2° | 100.0 |
| 8.6 ± 0.2° | 27.6 |
| 11.5 ± 0.2° | 19.2 |
| 13.3 ± 0.2° | 41.3 |
| 13.9 ± 0.2° | 12.0 |
| 14.5 ± 0.2° | 10.7 |
| 16.2 ± 0.2° | 26.2 |
| 17.4 ± 0.2° | 10.5 |
| 19.5 ± 0.2° | 17.7 |
| 23.3 ± 0.2° | 11.1 |
| 24.6 ± 0.2° | 19.2 |
| 25.3 ± 0.2° | 18.7 |
| 26.1 ± 0.2° | 13.4 |
| 26.9 ± 0.2° | 16.2 |
| 27.9 ± 0.2° | 10.5 |
| 31.7 ± 0.2° | 12.8 |

Non-restrictively, in one typical embodiment of the present invention, the X-ray powder diffraction pattern of Form 1 is shown in FIG. 2.

The Fourier transform infrared spectrum of Form 1 has characteristic peaks at wave numbers of 1485, 1461, 1370, 1349, 1287, 1104, 1066, 943, 831 and 758 cm$^{-1}$.

According to an objective of the present invention, the present invention provides a preparation method of Form 1, characterized in that, the preparation method is selected from any one of the following methods, comprising:

(1) Forming a suspension of ozanimod in $C_4$ to $C_6$ ether, $C_1$ to $C_4$ alcohol, cyclic ether, nitrile, water, alkane, nitromethane or their solvent mixture, stirring for crystallization, then separating and drying to obtain Form 1. The stirring time is from 1 day to 2 days.

Preferably, the solvent is selected from the group consisting of diethyl ether, ethanol, acetonitrile, water, methanol, dichloromethane, nitromethane, heptane, and any mixture thereof.

Preferably, the operation temperature of the preparation method is from 10° C. to 40° C., more preferably room temperature.

Preferably, the drying temperature is from 10° C. to 60° C., more preferably from 10° C. to 40° C.

Preferably, the drying time is from 10 to 48 hours, more preferably from 10 to 24 hours.

Preferably, the weight to volume ratio of ozanimod to solvent is from 5 mg:1 mL to 100 mg:1 mL, more preferably from 20 mg:1 mL to 50 mg:1 mL.

(2) Forming a solution of ozanimod in a mixed solvent of nitromethane and alkane or in a mixed solvent of $C_1$ to $C_4$ alcohol and alkane or in a mixed solvent of cyclic ether and water, then evaporating to obtain Form 1.

Preferably, the mixed solvent is selected from the group consisting of nitromethane and heptane mixture, acetonitrile and water mixture, and dichloromethane and methanol mixture.

Preferably, the evaporation temperature is from 10° C. to 60° C., more preferably from 10° C. to 40° C.

Preferably, the concentration of ozanimod solution is 0.5 to 1.0 times of the solubility of ozanimod in the selected solvent, more preferably 0.8 to 1.0 times.

(3) Heating a solution of ozanimod in nitromethane, haloalkane, cyclic ether, acetonitrile, or any mixture thereof to clear, stirring at low temperature for crystallization, then separating and drying to obtain Form 1.

Preferably, the solvent is selected from the group consisting of nitromethane, acetonitrile, chloroform, and any mixture thereof.

Preferably, the operation temperature of the preparation method is from 40° C. to 70° C., more preferably from 50° C. to 70° C.

Preferably, the low temperature is from −10° C. to 30° C., more preferably from −10° C. to 0° C.

Preferably, the drying temperature is from 10° C. to 40° C., more preferably from 10° C. to 30° C.

Preferably, the drying time is from 10 to 48 hours, more preferably from 10 to 24 hours.

Preferably, the weight to volume ratio of ozanimod to solvent is from 5 mg:1 mL, to 15 mg:1 mL, more preferably from 7 mg:1 mL to 15 mg:1 mL Form 1 of the present invention has the following advantageous properties.

(1) Compared to the known amorphous form, Form 1 of the present invention has higher crystallinity.

(2) After having been placed at 50° C. for 1 day, the known amorphous form of ozanimod showed diffraction peaks, while Form 1 of the present invention remained unchanged. Therefore, Form 1 of the present invention is more stable.

(3) After having been placed at room temperature and desiccators with relative humidity ranging from 10% to 90% for 4 months respectively, Form 1 of the present invention remained unchanged in appearance, XRPD and the melting point.

Form 1 of the present invention has good stability. Form 1 can better ensure the quality of the active ingredients and formulations containing ozanimod, avoiding and reducing the quality, safety and stability issues during pharmaceutical production and/or storage, such as content uniformity and impurity issues, avoiding special and expensive package.

According to an objective of the present invention, the present invention provides ozanimod Form 2 (herein after referred to as "Form 2").

Form 2 is anhydrous, and its chemical structure is shown in the following Formula (I):

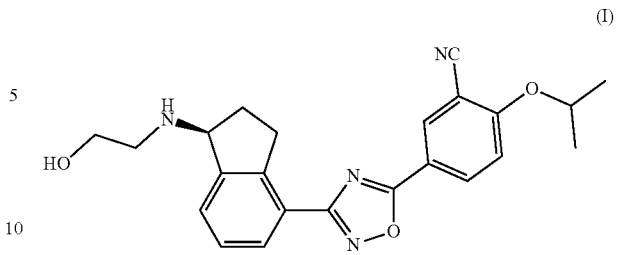

(I)

Using Cu-Kα radiation, the X-ray powder diffraction pattern of Form 2, expressed as 2θ angles, has the following characteristic peaks: 4.2±0.2°, 16.0±0.2°, 23.4±0.2°, 26.7±0.2° and 30.3±0.2°.

More preferably, the X-ray powder diffraction pattern of Form 2, expressed as 2θ angles, has the following characteristic peaks: 4.2±0.2°, 16.0±0.2°, 17.9±0.2°, 18.6±0.2°, 19.1±0.2°, 20.5±0.2°, 23.4±0.2°, 26.7±0.2° and 26.9±0.2°.

Further preferably, the X-ray powder diffraction pattern of Form 2, expressed as 2θ angles, has the following characteristic peaks with their relative intensities:

| Diffraction angel 2θ | Relative intensity % |
| --- | --- |
| 4.2 ± 0.2° | 24.7 |
| 8.2 ± .2° | 7.9 |
| 16.0 ± 0.2° | 12.3 |
| 17.9 ± 0.2° | 9.1 |
| 18.6 ± 0.2° | 10.1 |
| 19.1 ± 0.2° | 10.1 |
| 20.5 ± 0.2° | 9.5 |
| 23.4 ± 0.2° | 100.0 |
| 26.7 ± 0.2° | 15.6 |
| 30.3 ± 0.2° | 34.3 |

Non-restrictively, in one typical embodiment of the present invention, the X-ray powder diffraction pattern of Form 2 is shown in FIG. 6.

The Fourier transform infrared spectrum of Form 2 has characteristic peaks at wave numbers of 1616, 1487, 1460, 1283, 1260, 1097, 1045, 939, 808 and 761 $cm^{-1}$.

According to an objective of the present invention, the present invention provides a preparation method of Form 2, characterized in that, the preparation method is selected from any one of the following methods, comprising:

(1) Forming a suspension of ozanimod in $C_1$ to $C_4$ alcohol, water, acetone, alkane, $C_3$ to $C_5$ ether, $C_2$ to $C_6$ ester, acetonitrile, toluene, dimethyl sulfoxide, or any mixture thereof, stirring for crystallization, then separating and drying to obtain Form 2. The stirring time is from 1 to 2 days.

Preferably, the solvent is selected from the group consisting of methanol, ethanol, water, acetone, dichloromethane, isopropyl ether, ethyl acetate, tetrahydrofuran, toluene, acetonitrile, dimethyl sulfoxide, heptane, and any mixture thereof.

Preferably, the operation temperature of the preparation method is from 10° C. to 40° C., more preferably room temperature.

Preferably, the stirring time is from 5 to 7 days.

Preferably, the drying temperature is from 10° C. to 60° C., more preferably from 10° C. to 40° C.

Preferably, the drying time is from 10 to 48 hours, more preferably from 10 to 24 hours.

Preferably, the weight to volume ratio of ozanimod to solvent is from 10 mg:1 mL to 100 mg:1 mL, more preferably from 20 mg:1 mL to 50 mg:1 mL.

(2) Forming a solution of ozanimod in $C_1$ to $C_4$ alcohol, $C_1$ to $C_4$ ketone, isopropyl acetate, toluene, dimethyl sulfoxide, or any mixture thereof, then evaporating to obtain Form 2.

Preferably, the solvent is selected from the group consisting of methanol, ethanol, acetone, isopropyl acetate, toluene, dimethyl sulfoxide, and any mixture thereof.

Preferably, the evaporation temperature is from 20° C. to 60° C., more preferably from 20° C. to 40° C.

Preferably, the concentration of ozanimod solution is 0.5 to 1.0 times of the solubility of ozanimod in the selected solvent, more preferably 0.8 to 1.0 times.

(3) Forming a solution of ozanimod in $C_2$ to $C_4$ alcohol, $C_2$ to $C_4$ ester, toluene, dimethyl sulfoxide, $C_3$ to $C_4$ ether, or any mixture thereof by heating to clear, stirring at low temperature for crystallization, then separating and drying to obtain Form 2.

Preferably, the $C_3$ to $C_4$ ether does not include cyclic ether.

Preferably, the solvent is selected from the group consisting of isopropanol, ethanol, water, isopropyl acetate, toluene, dimethyl sulfoxide, isopropyl ether, and any mixture thereof.

Preferably, the operation temperature of the preparation method is from 40° C. to 70° C., more preferably from 50° C. to 70° C.

Preferably, the low temperature is from −10° C. to 30° C., more preferably from −10° C. to 0° C.

Preferably, the drying temperature is from 10° C. to 40° C., more preferably from 10° C. to 30° C.

Preferably, the drying time is from 10 to 48 hours, more preferably from 10 to 24 hours.

Preferably, the weight to volume ratio of ozanimod to solvent is from 5 mg:1 mL to 20 mg:1 mL, more preferably from 7 mg:1 mL to 20 mg:1 mL Form 2 in the present invention has the following advantageous properties.

(1) Compared to the known amorphous ozanimod solids, Form 2 has higher crystallinity.

(2) After having been stirred in water for 3 days, Form 2 of the present invention remained unchanged, while the known amorphous form of ozanimod turned to Form 2. This property makes Form 2 of the present invention more suitable for wet granulation of a solid formulation or an oral suspension dosage form. It is more likely to remain stable during pharmaceutical production and/or storage (3) After having been placed at room temperature, desiccators with relative humidity ranging from 10% to 90% for 4 months respectively, Form 2 of the present invention remained unchanged in appearance, XRPD and melting point.

Form 2 of the present invention has good stability. Form 2 can better ensure the quality of the active ingredients itself and formulations containing ozanimod, avoiding and reducing the quality, safety and stability issues during pharmaceutical production and/or storage, such as content uniformity and impurity issues, avoiding special and expensive package.

According to an objective of the present invention, the present invention provides ozanimod Form 3 (herein after referred to as "Form 3").

Form 3 is anhydrous, and its chemical structure is shown in the following formula (I):

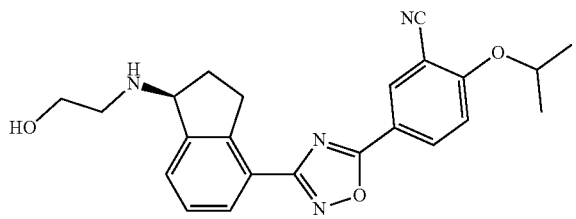

(I)

Using Cu-Kα radiation, the X-ray powder diffraction pattern of Form 3, expressed as 2θ angles, has the following characteristic peaks: 4.6±0.2°, 9.1±0.2°, 13.6±0.2°, 18.1±0.2° and 22.7±0.2°.

More preferably, the X-ray powder diffraction pattern of Form 3, expressed as 2θ angles, has the following characteristic peaks: 4.6±0.2°, 8.0±0.2°, 9.1±0.2°, 11.2±0.2°, 13.1±0.2°, 13.6±0.2°, 18.1±0.2°, 19.3±0.2°, 22.7±0.2° and 26.2±0.2°.

Further preferably, the X-ray powder diffraction pattern of Form 3, expressed as 2θ angles, has the following characteristic peaks with their relative intensities:

| Diffraction angel 2θ | Relative intensity % |
|---|---|
| 4.6 ± 0.2° | 100.0 |
| 8.0 ± 0.2° | 1.2 |
| 9.1 ± 0.2° | 10.8 |
| 11.2 ± 0.2° | 2. |
| 13.1 ± 0.2° | 2.6 |
| 13.6 ± 0.2° | 9.6 |
| 13.9 ± 0.2° | 1.3 |
| 17.2 ± 0.2° | 0.4 |
| 18.1 ± 0.2° | 4.5 |
| 19.3 ± 0.2° | 1.0 |
| 22.7 ± 0.2° | 5.3 |
| 23.4 ± 0.2° | 0.4 |
| 25.3 ± 0.2° | 0.3 |
| 26.2 ± 0.2° | 1.2 |
| 26.8 ± 0.2° | 0.3 |

Non-restrictively, in one typical embodiment of the present invention, the X-ray powder diffraction pattern of Form 3 is shown in FIG. 10.

The Fourier transform infrared spectrum of Form 3 has characteristic peaks at wave numbers of 1616, 1487, 1459, 1350, 1284, 1151, 1126, 1103, 943 and 758 cm$^{-1}$.

According to an objective of the present invention, the present invention provides a preparation method of Form 3, characterized in that, the preparation method is selected from any one of the following methods, comprising:

Forming a solution of ozanimod in ethyl acetate, cyclic ether, acetonitrile, haloalkane, or any mixture thereof, then evaporating to obtain Form 3.

Preferably, the solvent is selected from the group consisting of ethyl acetate, tetrahydrofuran, acetonitrile, dichloromethane, and any mixture thereof.

Preferably, the evaporation temperature is from 0° C. to 40° C., more preferably room temperature.

Preferably, the concentration of ozanimod solution is 0.5 to 1.0 times of the solubility of ozanimod in the selected solvent, more preferably 0.8 to 1.0 times.

Form 3 of the present invention has the following advantageous properties.

(1) Compared to the known amorphous solids, Form 3 has higher crystallinity.

(2) After having been placed at room temperature and at a 97% relative humidity environment for 3 days respectively, Form 3 of the present invention remained unchanged, while the known amorphous form of ozanimod turned to Form 3.

This indicates Foiin 3 of the present invention has good stability; it can better ensure the quality of the active ingredients itself and formulations containing ozanimod, avoiding and reducing the quality, safety and stability issues during pharmaceutical production and/or storage, such as content uniformity and impurity issues, avoiding special and expensive package.

The present inventors also provide ozanimod Form 4 (herein after referred to as "Form 4") and ozanimod Form 5 (herein after referred to as "Form 5") and their preparation methods.

Comparing to the known solid form of ozanimod in the prior art, Form 4 and Form 5 have at least one or more advantageous properties, such as higher crystallinity, better solubility, faster dissolution rate, better crystal morphology, better thermal stability and storage stability, lower hygroscopicity, better flowability and processibility.

Using Cu-Kα radiation, the X-ray powder diffraction pattern of Form 4, expressed as 2θ angles, has the following characteristic peaks: 4.3±0.2°, 7.5±0.2°, 10.6±0.2°, 12.2±0.2°, 12.9±0.2°, 17.3±0.2°, 17.7±0.2°, 18.3±0.2°, 21.6±0.2°, 22.5±0.2° and 24.6±0.2°.

According to an objective of the present invention, the present invention provides a preparation method of Form 4, characterized in that, the preparation method is selected from any one of the following methods, comprising:

(1) Forming a suspension of ozanimod in methanol, stiring at certain temperature for crystallization, then separating and drying to obtain Form 4. Preferably, the stirring temperature is from 10° C. to 40° C., the stirring time is from 3 to 7 days, and the drying temperature is from 10° C. to 40° C.

(2) Heating a solution of ozanimod in methanol or a solvent mixture containing methanol to clear, stirring at low temperature for crystallization, then separating and drying to obtain Form 4. Preferably, the solution is heated to a temperature from 50° C. to 60° C., the low temperature is from −10° C. to 10° C., and the drying temperature is from 10° C. to 40° C.

Using Cu-Kα radiation, the X-ray powder diffraction pattern of Form 5, expressed as 2θ angles, has the following characteristic peaks: 6.7±0.2°, 6.9±0.2°, 10.3±0.2°, 10.7±0.2°, 11.3±0.2°, 12.7±0.2°, 13.1±0.2°, 16.6±0.2°, 18.9±0.2°, 20.6±0.2° and 22.6±0.2°.

According to an objective of the present invention, the present invention provides a preparation method of Form 5, comprising: Forming a suspension of ozanimod in butanone or a solvent mixture containing butanone, stirring at certain temperature for crystallization, then separating and drying to obtain Form 5. Preferably, the operation temperature of the preparation method is from −10° C. to 60° C.

Compared to the known solid form of ozanimod in the prior art, Form 1, Form 2, Form 3, Form 4 and Form 5 of the present invention have at least one or more advantageous properties, such as higher crystallinity, better solubility, faster dissolution rate, better crystal morphology, better thermal stability and storage stability, low hygroscopicity, higher API content, better flowability and processability for formulation, and its room temperature or low temperature preparation temperature makes it easy for product industrialization.

In the preparation methods of Form 1, Form 2, Form 3, Form 4 and Form 5 of the present invention:

Unless otherwise specified, room temperature refers to 10° C. to 30° C.

Cyclic ether may be tetrahydrofuran or dioxane.

Haloalkane may be dichloromethane, chloroform, or carbon tetrachloride.

Stirring may be performed by routine methods in the field, such as magnetic stirring or mechanical stirring. The stirring speed is 50 to 1800 r/min, preferably 300 to 900 r/min.

Separation may be performed by routine methods in the field such as centrifugation or filtration. Preferred method is vacuum filtration, generally at a pressure less than atmospheric pressure at room temperature, preferably less than 0.09 MPa.

Drying may be performed by routine methods in the field, such as room temperature drying, blast drying or vacuum drying. Drying is performed under reduced pressure or atmospheric pressure, pressure less than 0.09 MPa is preferred. Drying instruments and methods are unrestricted and can be fume hood, blast oven, spray drying, fluidized bed drying or vacuum oven.

In the present invention, the starting material ozanimod can be obtained by preparation referencing the methods described in examples 0388-0399 in patent CN1027621001B or it can be purchased commercially. This reference is incorporated into this application by reference in its entireties.

Furthermore, the present invention provides a pharmaceutical composition, which comprises a therapeutically and/or preventively effective amount of active pharmaceutical ingredient selected from one or more crystalline forms of ozanimod of the present invention or the crystalline forms prepared by using preparation methods of the present invention, and at least one pharmaceutically acceptable carrier or additive. The novel crystalline forms of ozanimod are Form 1, Form 2 and Form 3. Moreover, the pharmaceutical composition may also comprise other pharmaceutically acceptable polymorphs (such as Form 4 and Form 5).

The excipients of pharmaceutical composition are known to those skilled in the field, the selection of the type, usage and amount of excipients is also known to those skilled in the field. They include carbohydrate, cellulose and its derivative, starch or modified starch, solid inorganics such as calcium phosphate, dicalcium phosphate, hydroxyapatite, calcium sulfate, calcium carbonate, semisolid such as lipids or paraffin wax, adhesive such as microcrystalline cellulose, ethyl cellulose, hydroxymethyl cellulose, hydroxypropyl methyl cellulose, hydroxyethyl cellulose, glidants such as colloidal silica dioxide, light anhydrous silicic acid, crystalline cellulose, talcum powder or magnesium stearate, disintegrants such assodium glycolate starch, crospovidone, croscarmellose, sodium carboxymethylcellulose, cornstarch, lubricant such as stearic acid, magnesium stearate, sodium stearyl fumarate, polyethyleneglycol.

The administrative routes of pharmaceutical compositions may be oral, intravenous injection, injection into tissue, transdermal, rectal, nasal dripping, etc. The pharmaceutical compositions may be made in certain dosage form depending on the administration routes or needs, such as in solid or liquid form. Solid oral dosage forms, such as tablets, granules, powders, pills and capsules; liquid oral dosage forms, such as solution, syrups, suspensions, dispersions and emulsions; injectable formulations, such as solutions, dispersions and lyophilized powders. The formulation may be suitable for immediate-release, sustained-release or controlled-release of the active ingredient. The formulation may be a regular, dispersible, chewable, orally soluble or rapidly dissolving form.

The pharmaceutical composition may be prepared by methods commonly known to those skilled in the art. In preparation of the pharmaceutical composition, Form 1, Form 2 or Form 3 of the present invention is mixed with one or more pharmaceutically acceptable excipients, optionally with other pharmaceutically acceptable polymorphs and amorphous form of ozanimod, optionally with one or more other active ingredients. Solid formulations may be prepared by direct mixing, granulation and other processes.

Furthermore, the present invention provides one or more crystalline forms of ozanimod or the crystalline forms prepared by using preparation methods of the present invention for treating and/or preventing one or more diseases or adverse conditions. The diseases are associated with modulation, activation, stimultion, inhibition or antagonization of selective sphingosine-1-phosphate (S1P) receptor. The diseases or adverse conditions include multiple sclerosis, transplant rejection or acute respiratory distress syndrome. The ozanimod crystalline forms include Form 1, Form 2, Form 3, Form 4, and Form 5 of the present invention.

Furthermore, the present invention provides a treating and/or preventing method for one or more diseases or adverse conditions, which consists of administrating to patients in need thereof a therapeutically and/or effectively amount of the ozanimod crystalline forms, their mixtures or pharmaceutical composition in the present invention. The diseases are associated with modulating, activation, stimultion, inhibition or antagonizing of selective sphingosine-1-phosphate (S1P) receptor. The diseases or adverse conditions include multiple sclerosis, ulcerative colitis, arthritis, transplant rejection or acute respiratory distress syndrome and so on. The ozanimod crystalline forms include Form 1, Form 2, Form 3, Form 4 and Form 5. The patients include but not limit to mammals.

EXAMPLES

The following examples help to further understand the present invention, but are not intended to limit the contents of the present invention.

Instruments and characterization methods:

X-ray powder diffraction (XRPD): performed on Bruker D8 Advance diffractometer.

The samples are tested at room temperature. The detailed testing conditions: scan range 3-40° 2θ, step size 0.02° 2θ, and speed 0.2 s/step.

The DSC data are collected on TA Instruments Q200 MDSC. The detailed testing conditions: place 1 mg to 10 mg sample into an aluminum pan with a pin-holed lid, ramp to 200° C.-250° C. at a rate of 10° C./min under the protection of dry $N_2$ at a purge rate of 40 mL/min.

The TGA data are collected on TA Instruments Q500 TGA. The detailed testing conditions: place 5 mg to 15 mg sample into an platinum pan, use high resolution method, ramp to 350° C. at a rate of 1.0° C./min under the protection of dry $N_2$ at a purge rate of 40 mL/min.

The Infrared spectrometry (IR) data are collected on Balker Tensor 27 equipped with an attenuated total reflection (ATR). The infrared spectra are collected over the range of 600 $cm^{-1}$ to 4000 $cm^{-1}$.

$^1$H Nuclear magnetic resonance spectrum ($^1$H-NMR) data are collected on Bruker Avance II DMX 300 MHz. Place 1 mg to 5 mg sample into NMR tube, dissolve with 0.5 mL deuterium reagents.

Unless particularly specified, all examples were conducted at room temperature, solvent ratio is volume ratio.

All reagents used in the examples were commercially purchased.

Preparation Example 1 (Prepare Ozanimod)

Ozanimod was prepared by referencing the methods described in examples 0388-0399 of patent document CN102762100B.

$^1$HNMR (300 MHz, CDCl3-CH3OD):

8.33 (d, 1H), 8.26 (dd, 1H), 7.99 (d, 1H), 7.47 (d, 1H), 7.33 (t, 1H), 7.07 (d, 1H), 4.74 (t, 1H), 4.27 (t, 1H), 3.62 (q, 2H), 3.37-3.32 (m, 1H), 3.18-3.10 (m, 1H), 2.79 (t, 2H), 2.48-2.37 (m, 1H), 1.92-1.85 (m, 1H), 1.40 (d, 6H), indicating that it is the known ozanimod.

Figure 1:
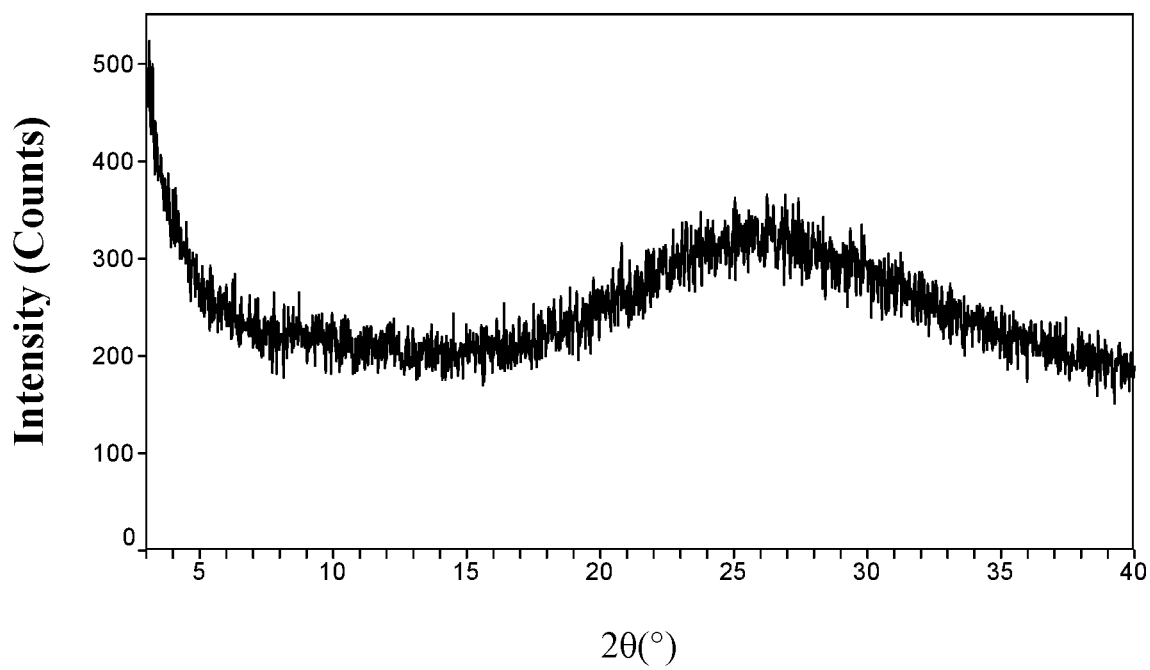
FIG. 1 is the XRPD pattern of the known ozanimod prepared by referencing the methods described in examples 0388-0399 of patent CN102762100B.

The X-ray powder diffraction pattern was shown in FIG. 1, indicating that the obtained ozanimod prepared by referencing the methods described in examples of patent document CN102762100B was amorphous.

Example 1

Took 15 mg of the ozanimod solid of Preparation Example 1, added 0.5 mL ethyl ether to obtain a suspension, stirred at room temperature for 2 days, vacuum filtrated, then vacuum dried at 40° C. for 10 hours to obtain 14.2 mg ozanimod Form 1; 16.4% yield.

Figure 2:
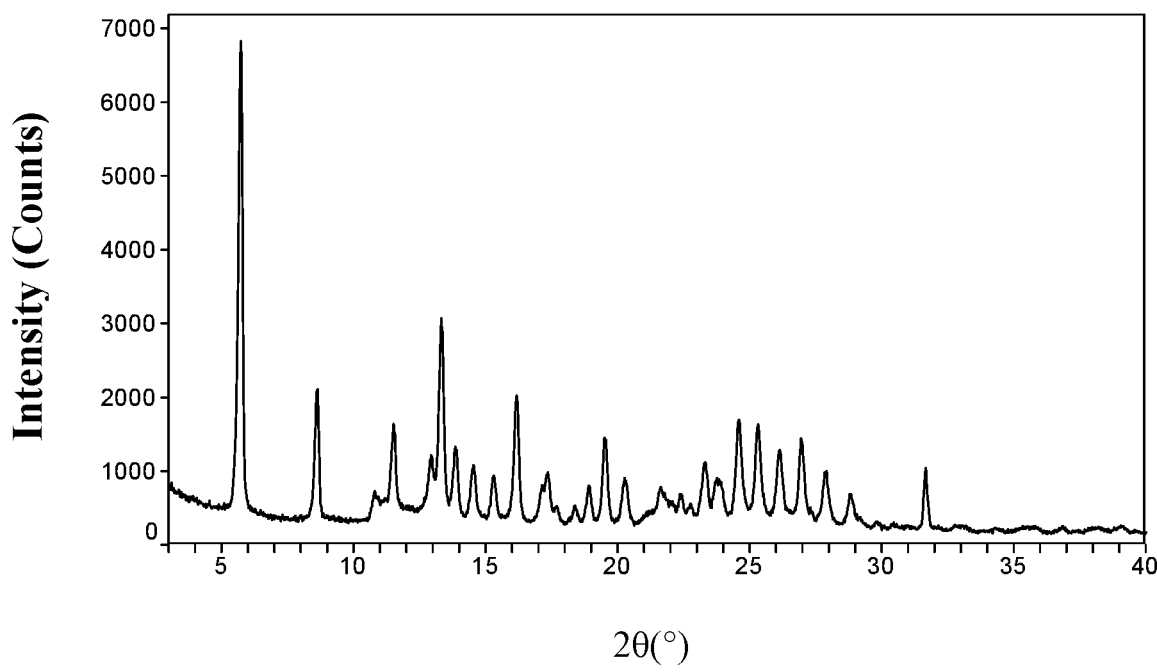
FIG. 2 is the XRPD pattern of ozanimod Form 1 prepared according to Example 2 of the present invention.
Figure 3:
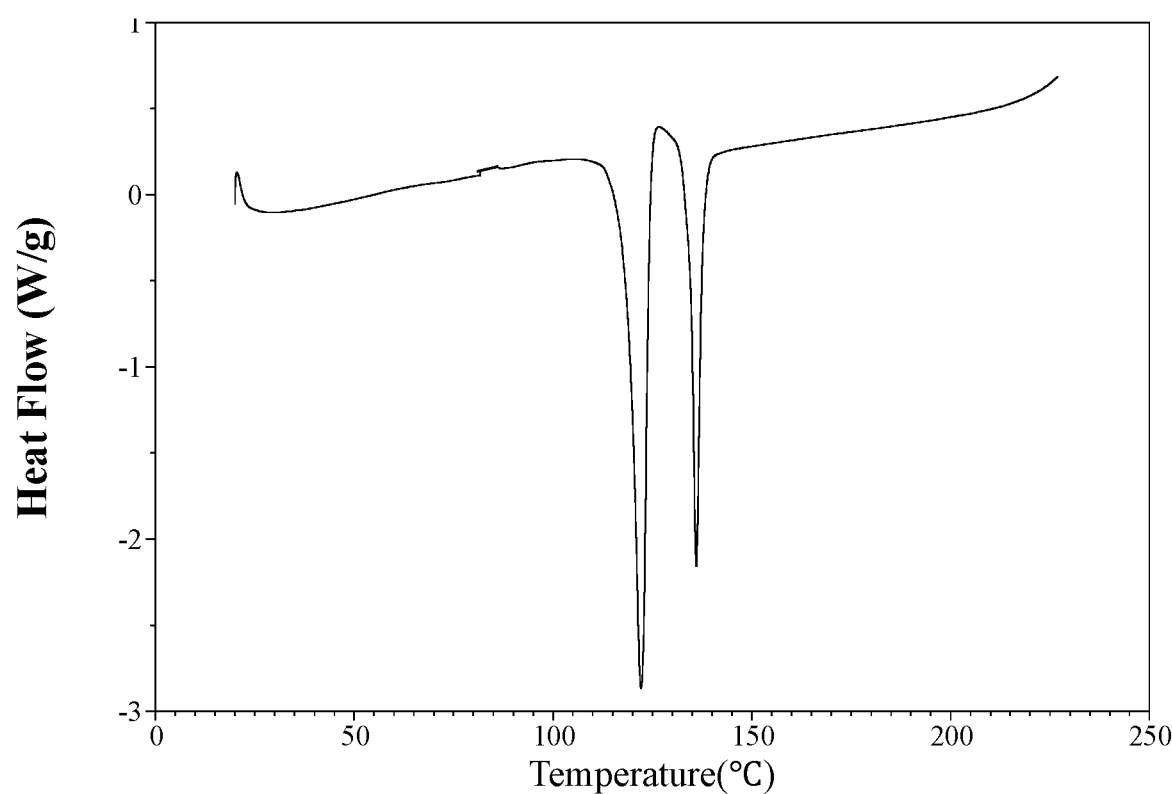
FIG. 3 is the DSC plot of ozanimod Form 1 prepared according to Example 2 of the present invention.
Figure 4:
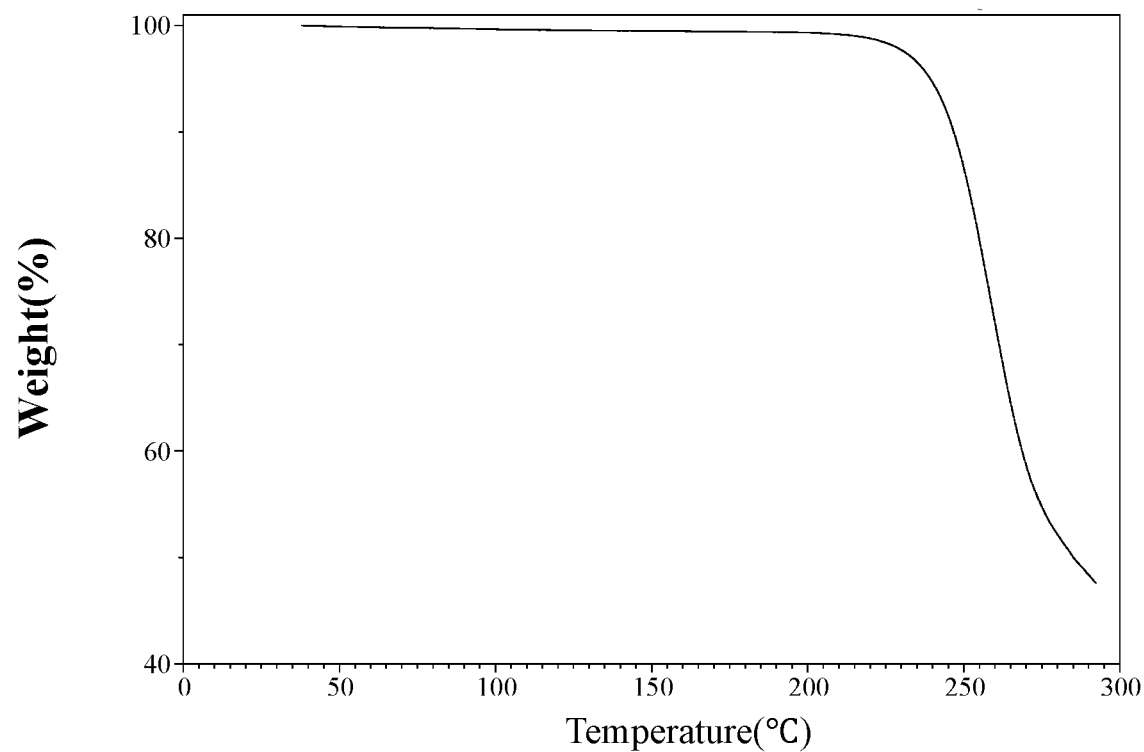
FIG. 4 is the TGA plot of ozanimod Form 1 prepared according to Example 2 of the present invention.
Figure 5:
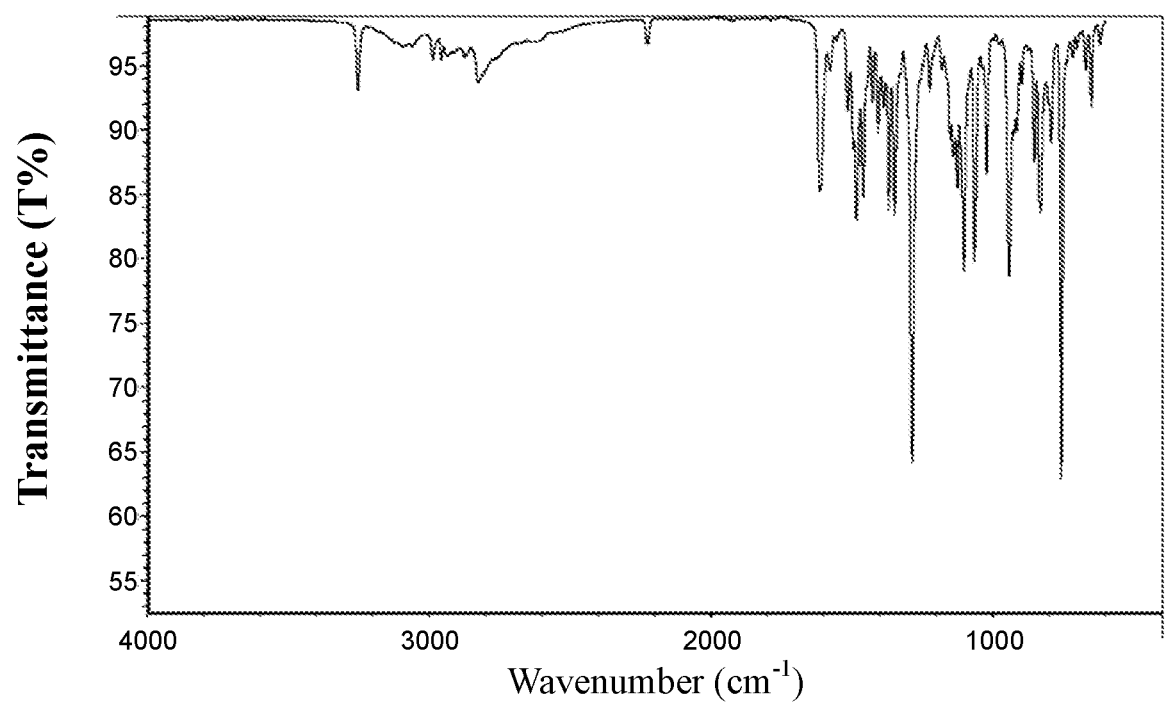
FIG. 5 is the IR spectrum of ozanimod Form 1 prepared according to Example 2 of the present invention.

The XRPD pattern is shown in FIG. 2.
The DSC plot is shown in FIG. 3.
The TGA plot is shown in FIG. 4.
The IR spectrum is shown in FIG. 5

Example 2

Took 15 mg of the ozanimod solid of Preparation Example 1, added 1.5 mL mixed solvents of acetonitrile:

water (1:2) to obtain a suspension, stirred at 40° C. for 2 days, vacuum filtrated, then vacuum dried at 60° C. for 48 hours to obtain 13.1 mg ozanimod Form 1; 87.3% yield.

Example 3

Took 20 mg of the ozanimod solid of Preparation Example 1, added 1.0 mL ethanol to obtain a suspension, stirred at room temperature for 1 day, vacuum filtrated, then vacuum dried at 10° C. for 24 hours to obtain 18.3 mg ozanimod Form 1; 91.5% yield.

Example 4

Ozanimod Form 1 can also be obtained by replacing the solvents in Example 3 with the following table.

| Experiment Number | Solvents |
| --- | --- |
| Experiment 1 | Methanol and dichloromethane |
| Experiment 2 | Methanol and nitromethane |
| Experiment 3 | Ethanol and n-heptane |
| Experiment 4 | Isopropyl ether and n-butanol |
| Experiment 5 | 1,4-Dioxane and water |
| Experiment 6 | Methylcyclohexane and methyl tert-butyl ether |

Example 5

Took 10 mg of the ozanimod solid of Preparation Example 1, added 1.0 mL mixed solvents of methanol:dichloromethane (1:9) to obtain a clear solution, evaporated at 20° C. to obtain ozanimod Form 1.

Example 6

Took 10 mg of the ozanimod solid of Preparation Example 1, added 3.0 mL mixed solvents of acetonitrile:water (2:1) to obtain a clear solution, evaporated at 40° C. to obtain ozanimod Form 1.

Example 7

Ozanimod Form 1 can also be obtained by replacing the solvents in Example 6 with the following table.

| Experiment Number | Solvents |
| --- | --- |
| Experiment 1 | Nitromethane and n-heptane |
| Experiment 2 | Nitromethane and methylcyclohexane |
| Experiment 3 | Ethanol and n-hexane |
| Experiment 4 | n-Butanol and methylcyclohexane |
| Experiment 5 | 1,4-Dioxane and water |
| Experiment 6 | Tetrahydrofuran and water |

Example 8

Took 15 mg of the ozanimod solid of Preparation Example 1, added 1.5 mL nitromethane at 70° C. to obtain a clear solution, stirred at −10° C. until precipitation occurs, then vacuum filtrated, and vacuum dried at 30° C. for 24 hours to obtain 13.8 mg ozanimod Form 1; 92.0% yield.

Example 9

Ozanimod Form 1 can also be obtained by replacing the solvents in Example 8 with the following table.

| Experiment Number | Solvents |
| --- | --- |
| Experiment 1 | Acetonitrile |
| Experiment 2 | Nitromethane and chloroform |
| Experiment 3 | 1,4-Dioxane |
| Experiment 4 | Nitromethane and dichloromethane |
| Experiment 5 | Acetonitrile and tetrahydrofuran |

XRPD patterns, DSC plots, TGA plots, IR spectra (not shown) of the samples prepared in Examples 2-9 are the same as or similar to that of the sample prepared in example 1, indicating the crystalline forms obtained in Examples 2-9 are the same as that of Example 1.

Example 10

Took 100 mg of the ozanimod solid of Preparation Example 1, added 2.0 mL ethanol to obtain a suspension, stirred at room temperature for 5 days, vacuum filtrated, then vacuum dried at 40° C. for 24 hours to obtain 96.8 mg ozanimod Form 2; 96.8% yield.

Figure 6:
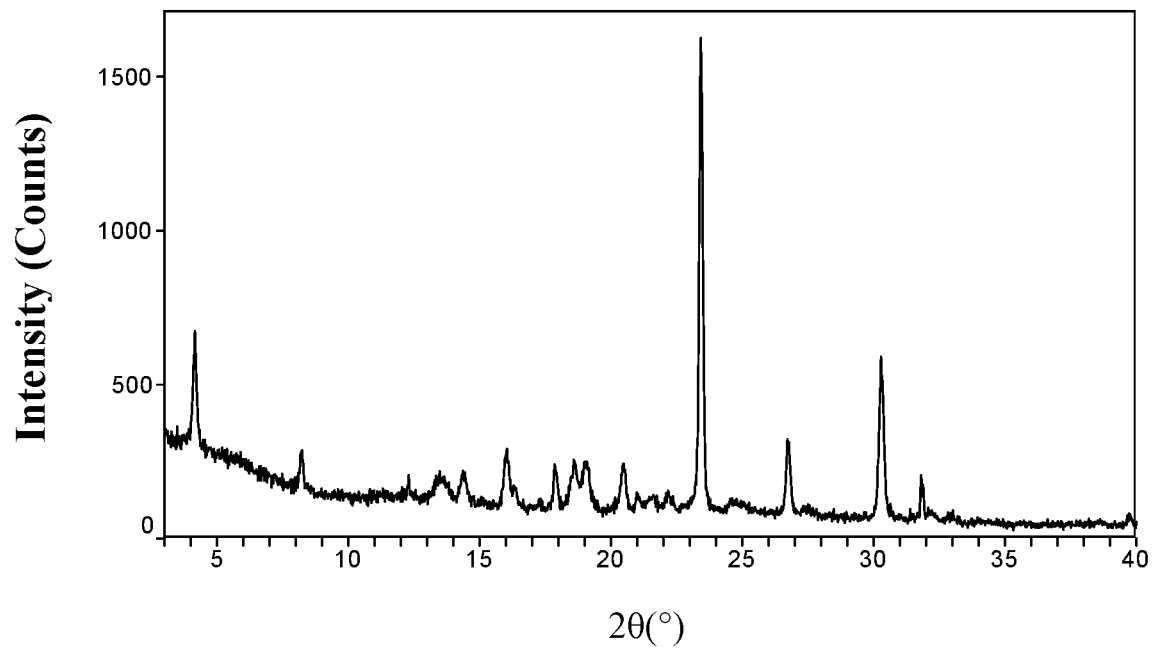
FIG. 6 is the XRPD pattern of ozanimod Form 2 prepared according to Example 10 of the present invention.
Figure 7:
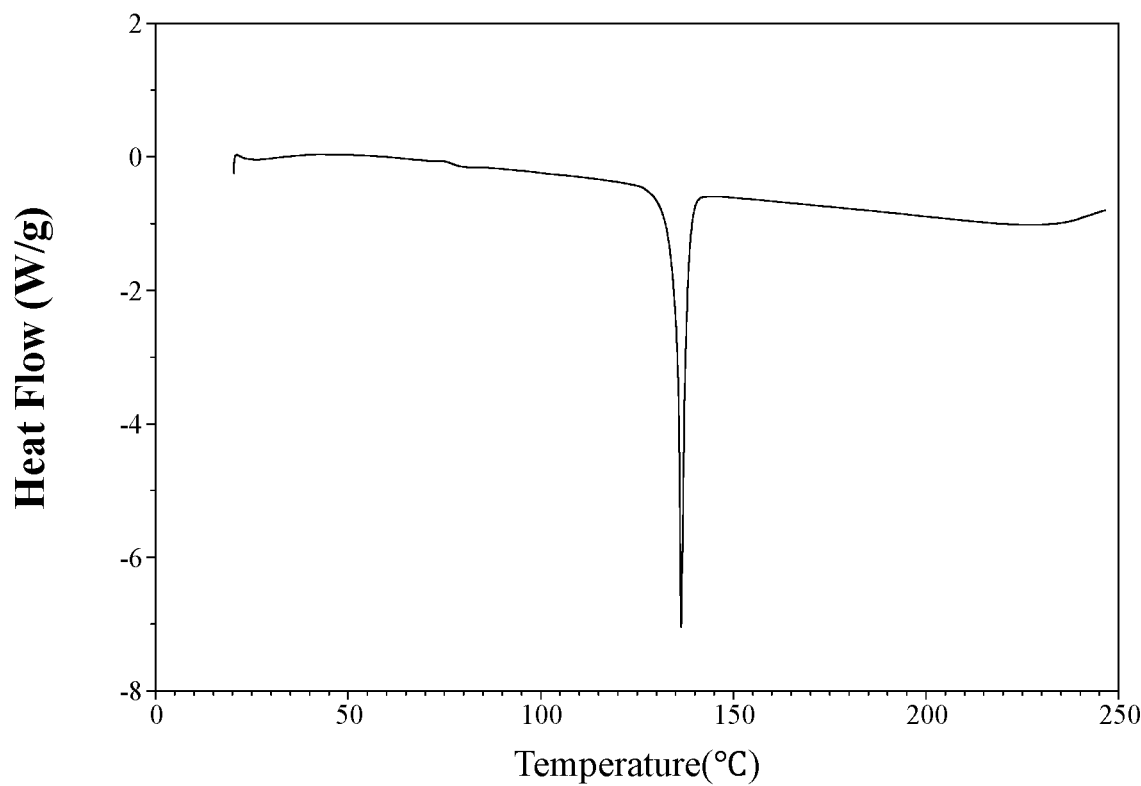
FIG. 7 is the DSC plot of ozanimod Form 2 prepared according to Example 10 of the present invention.
Figure 8:
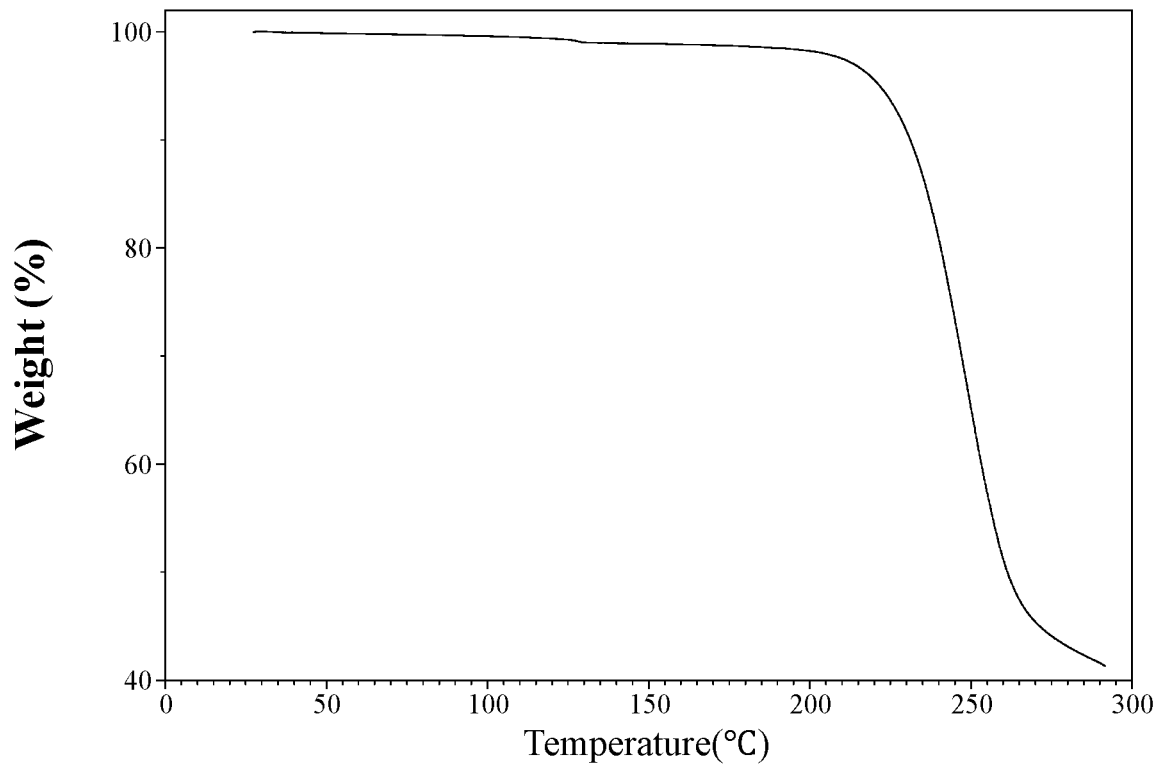
FIG. 8 is the TGA plot of ozanimod Form 2 prepared according to Example 10 of the present invention.
Figure 9:
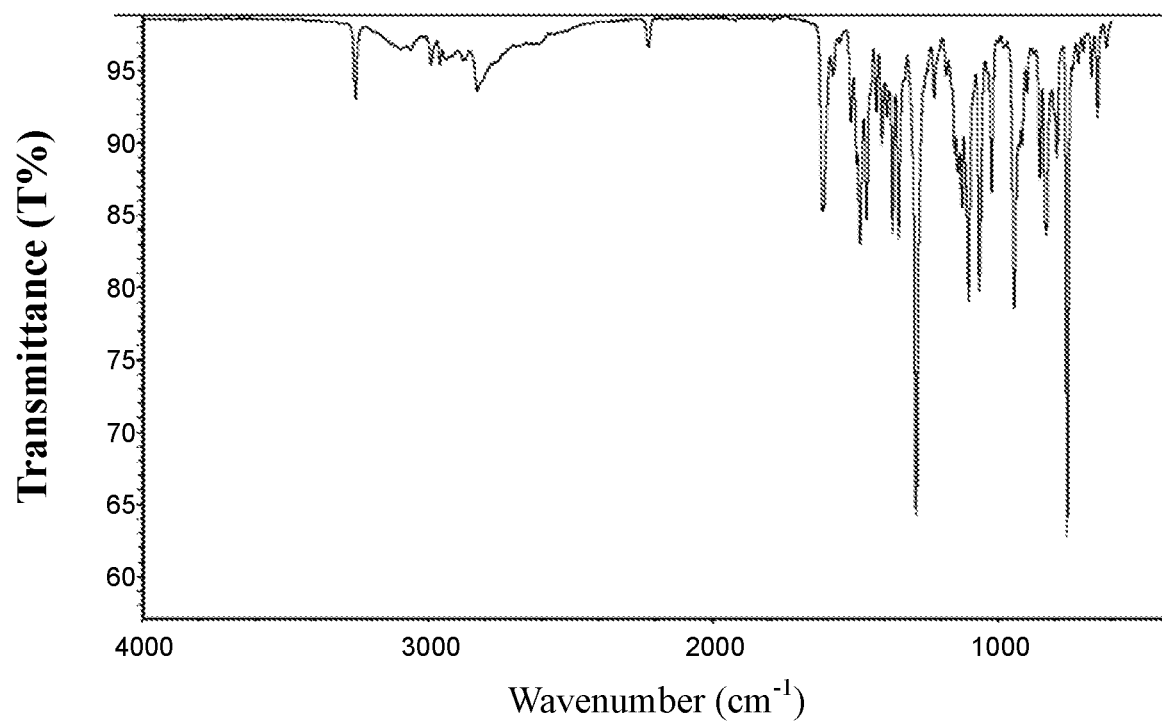
FIG. 9 is the IR spectrum of ozanimod Form 2 prepared according to Example 10 of the present invention.

The XRPD pattern is shown in FIG. 6.
The DSC plot is shown in FIG. 7.
The TGA plot is shown in FIG. 8.
The IR spectrum is shown in FIG. 9.

Example 11

Took 15 mg of the ozanimod solid of Preparation Example 1, added 0.5 mL acetone to obtain a suspension, stirred at room temperature for 7 days, vacuum filtrated, then vacuum dried at 10° C. for 10 hours to obtain 14.1 mg ozanimod Form 2; 94.0% yield.

Example 12

Took 15 mg of the ozanimod solid of Preparation Example 1, added 0.2 mL isopropyl ether to obtain a suspension, stirred at 40° C. for 3 days, vacuum filtrated, then vacuum dried at 60° C. for 48 hours to obtain 12.1 mg ozanimod Form 2; 80.6% yield.

Example 13

Ozanimod Form 2 can also be obtained by replacing the solvents in Example 12 with the following table.

| Experiment Number | Solvents |
| --- | --- |
| Experiment 1 | Methanol and water |
| Experiment 2 | Water |
| Experiment 3 | Dichloromethane and ethyl acetate |
| Experiment 4 | Tetrahydrofuran and toluene |
| Experiment 5 | Dimethyl sulfoxide and acetonitrile |
| Experiment 6 | Ethanol and methylcyclohexane |
| Experiment 7 | Isopropanol, propyl propionate and ethyl ether |
| Experiment 8 | Methanol and methyl formate |

Example 14

Took 5 mg of the ozanimod solid of Preparation Example 1, added 1.0 mL 2-butanol to obtain a clear solution, evaporated at 30° C. to obtain ozanimod Form 2.

Example 15

Took 5 mg of the ozanimod solid of Preparation Example 1, added 1.0 mL toluene to obtain a clear solution, evaporated at 50° C. to obtain ozanimod Form 2.

Example 16

Ozanimod Form 2 can also be obtained by replacing the solvents in Example 15 with the following table.

| Experiment Number | Solvents |
|---|---|
| Experiment 1 | Methanol |
| Experiment 2 | Ethanol |
| Experiment 3 | Acetone and dimethyl sulfoxide |
| Experiment 4 | Trifluoroethanol and butanone |
| Experiment 5 | Toluene and isopropyl acetate |

Example 17

Took 15 mg of the ozanimod solid of Preparation Example 1, added 0.75 mL mixed solvents of ethanol:water (4:1) at 50° C. to obtain a clear solution, stirred at −10° C. until precipitation occurs, then vacuum filtrated, and vacuum dried at 30° C. for 24 hours to obtain 14.1 mg ozanimod Form 2; 94.0% yield.

Example 18

Ozanimod Form 2 can also be obtained by replacing the solvents in Example 17 with the following table.

| Experiment Number | Solvents |
|---|---|
| Experiment 1 | Isopropanol and toluene |
| Experiment 2 | Dimethyl sulfoxide and isopropyl ether |
| Experiment 3 | Methyl formate and 2-butanol |
| Experiment 4 | Isopropyl acetate and ethyl ether |
| Experiment 5 | Trifluoroethanol and propyl propionate |

XRPD patterns, DSC plots, TGA plots, IR spectra (not shown) of the samples prepared in Examples 11~18 are the same as or similar to that of the sample prepared in Example 10, indicating the crystalline forms obtained in Examples 11~18 are the same as that of Example 10.

Example 19

Took 5 mg of ozanimod Form 2 in Example 10, added 2.0 mL ethyl acetate to obtain a clear solution, evaporated at room temperature to obtain ozanimod Form 3.

Figure 10:
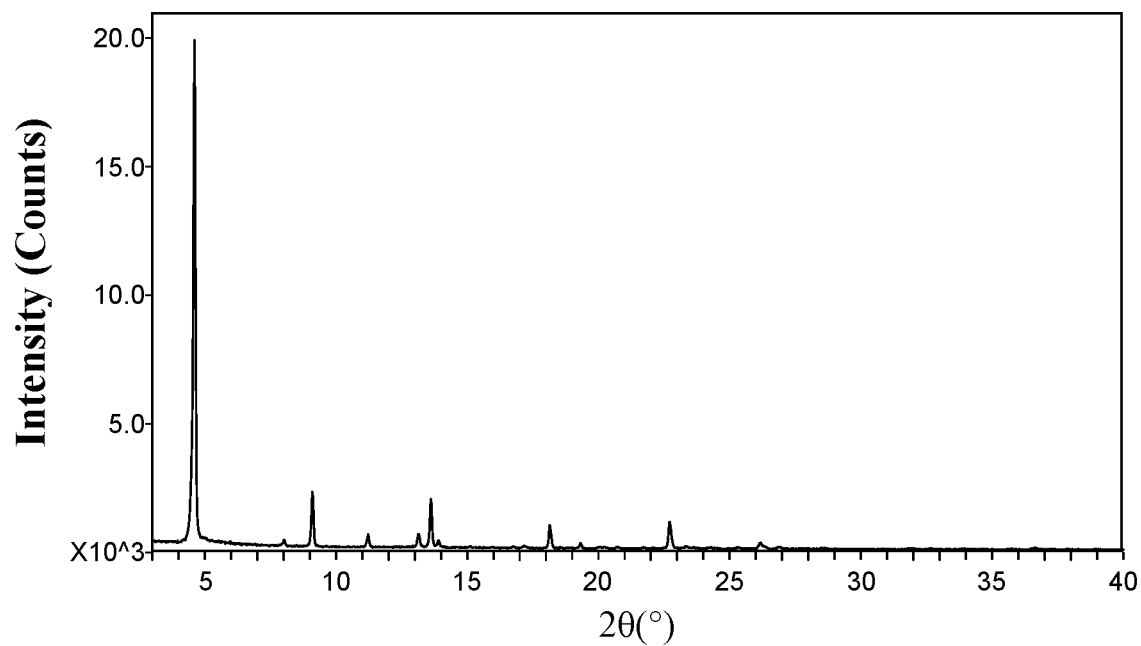
FIG. 10 is the XRPD pattern of ozanimod Form 3 prepared according to Example 19 of the present invention.
Figure 11:
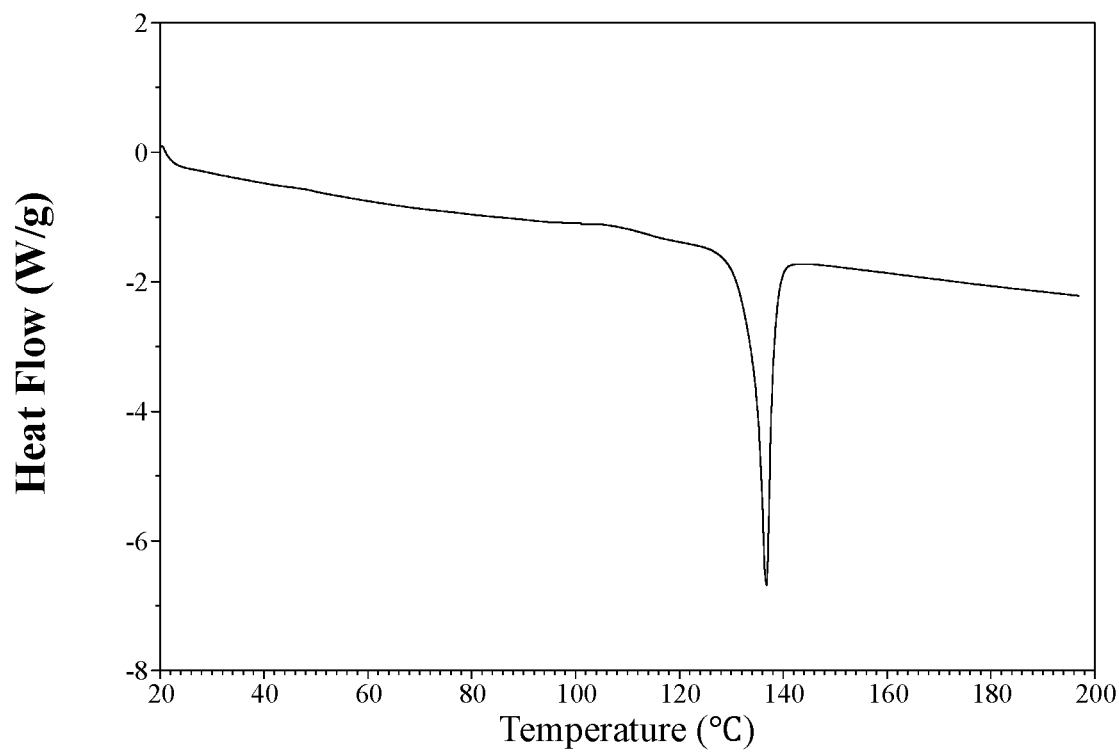
FIG. 11 is the DSC plot of ozanimod Form 3 prepared according to Example 19 of the present invention.
Figure 12:
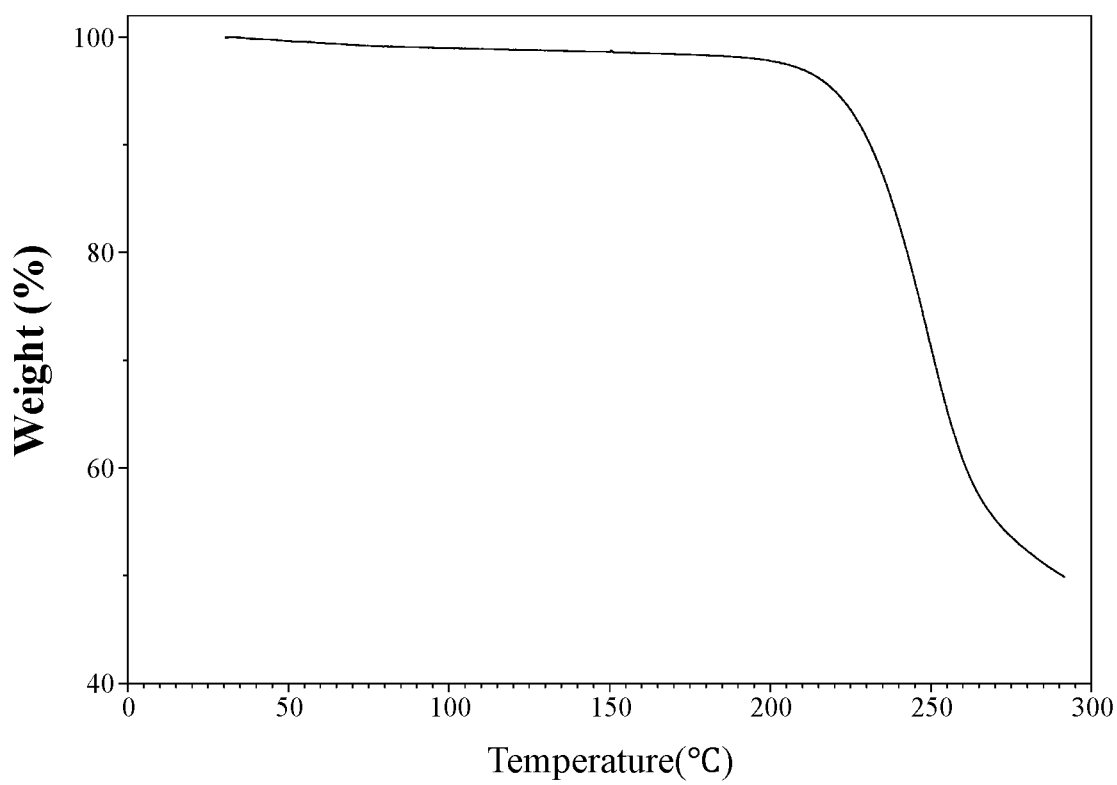
FIG. 12 is the TGA plot of ozanimod Form 3 prepared according to Example 19 of the present invention.
Figure 13:
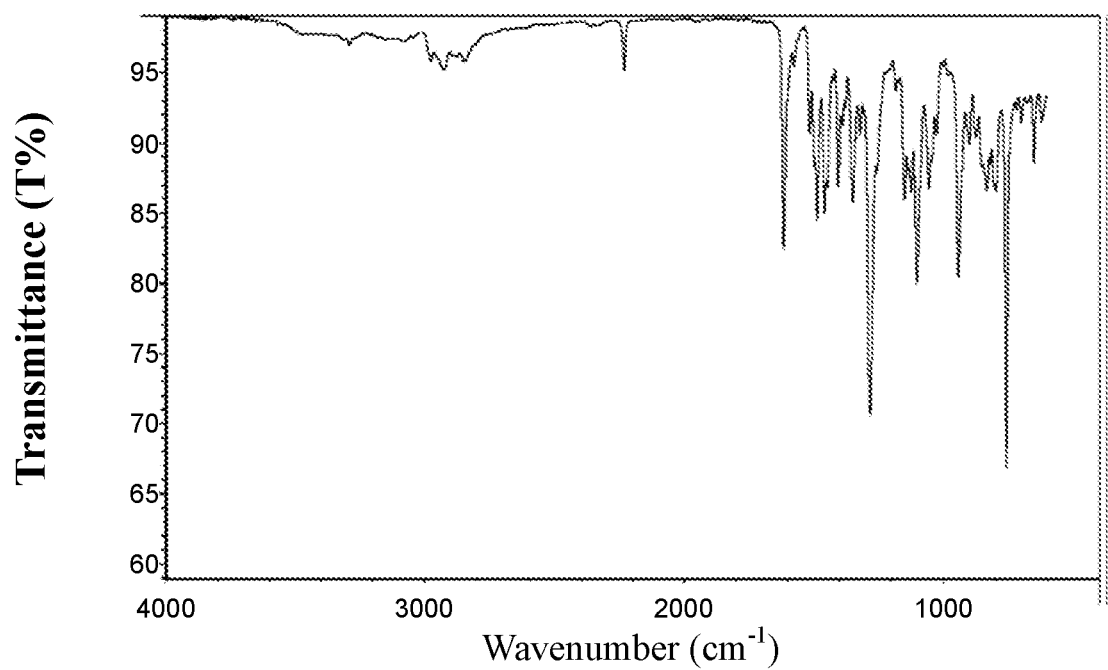
FIG. 13 is the IR spectrum of ozanimod Form 3 prepared according to Example 19 of the present invention.

The XRPD pattern is shown in FIG. 10.
The DSC plot is shown in FIG. 11.
The TGA plot is shown in FIG. 12.
The IR spectrum is shown in FIG. 13.

Example 20

Took 5 mg of ozanimod solid of Preparation Example 1, added 0.2 mL tetrahydrohuran to obtain a clear solution, evaporated at 0° C. to obtain ozanimod Form 3.

Example 21

Took 5 mg of ozanimod of Preparation Example 1, added 1.0 mL acetonitrile to obtain a clear solution, evaporated at 40° C. to obtain ozanimod Form 3.

Example 22

Took 5 mg of ozanimod solid of Preparation Example 1, added 0.6 mL mixed solvents of dichloromethane:tetrahydrofuran (1:1) to obtain a clear solution, evaporated at 5° C. to obtain ozanimod Form 3.

Example 23

Took 5 mg of ozanimod solid of Preparation Example 1, added 1.5 mL mixed solvents of chloroform:1,4-dioxane (2:1) to obtain a clear solution, evaporated at 36° C. to obtain ozanimod Form 3.

XRPD patterns, DSC plots, TGA plots, IR spectra (not shown) of the samples prepared in Examples 20 to 23 are the same as or similar to that of the sample prepared in Example 19, indicating the crystalline forms obtained in Examples 20 to 23 are the same as that of Example 19.

Example 24

Took 15 mg of ozanimod solid of Preparation Example 1, added 0.5 mL methanol to obtain a suspension, stirred at room temperature for 7 days, vacuum filtrated, then vacuum dried at 10° C. for 24 hours to obtain ozanimod Form 4.

Figure 14:
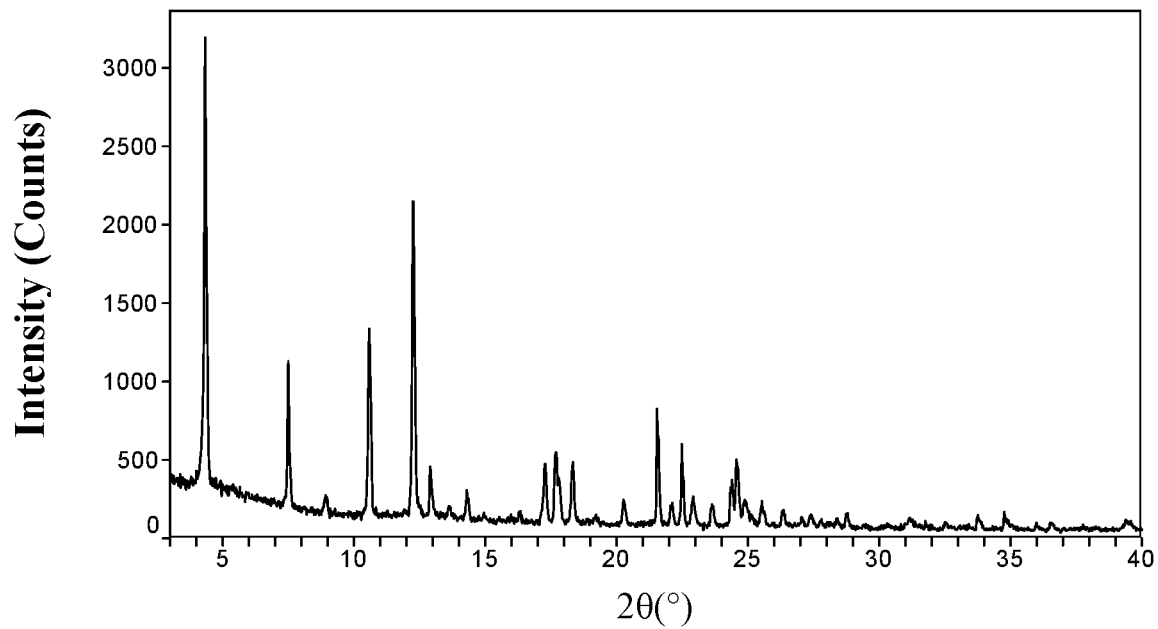
FIG. 14 is the XRPD pattern of ozanimod Form 4 prepared according to Example 24 of the present invention.

The XRPD pattern is shown in FIG. 14.

Example 25

Took 15 mg of ozanimod solid of Preparation Example 1, added 0.4 mL mixed solvents of methanol:ethyl acetate (2:3) at 60° C. to obtain a clear solution, stirred at −10° C. until precipitation occurred, then vacuum filtrated, and vacuum dried at 40° C. for 24 hours to obtain ozanimod Form 4.

The XRPD pattern is the same as the sample prepared in Example 24 (not shown), the crystal form is ozanimod Form 4.

Example 26

Took 15 mg of ozanimod solid of Preparation Example 1, added 0.5 mL butanone to obtain a suspension, stirred at room temperature for 3 days, vacuum filtrated, then vacuum dried at 30° C. for 16 hours to obtain ozanimod Form 5.

Figure 15:
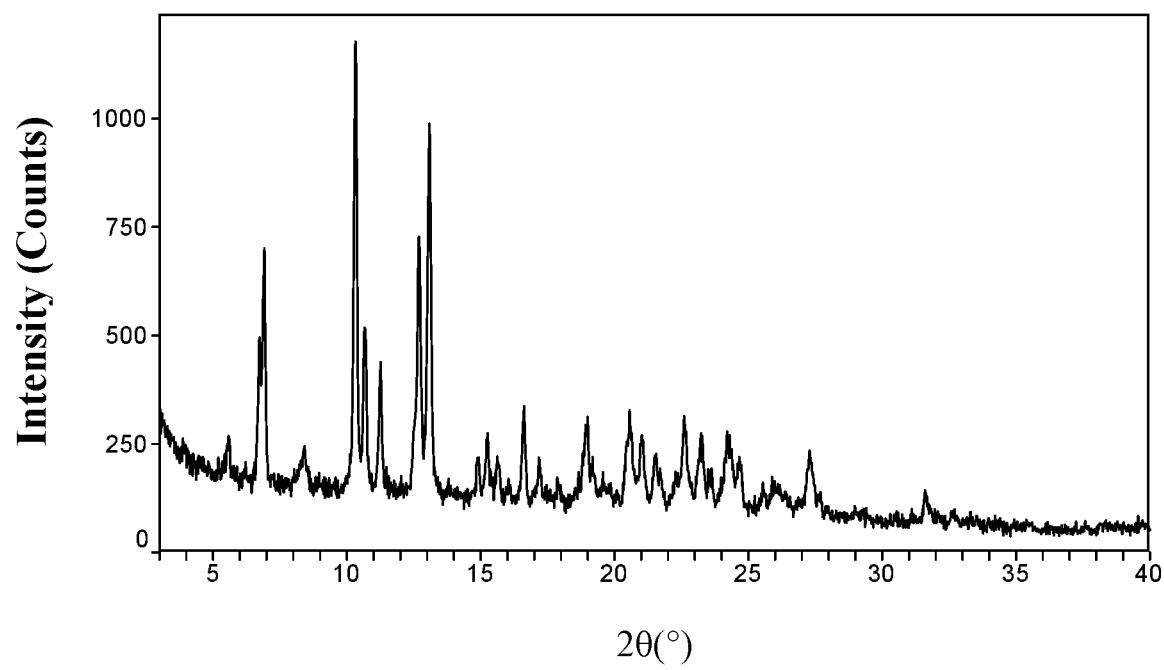
FIG. 15 is the XRPD pattern of ozanimod Form 5 prepared according to Example 26 of the present invention.

The XRPD pattern is shown in FIG. 15.

Example 27

A typical tablet prepared by conventional tableting techniques contains:

| Core: | |
|---|---|
| Ozanimod Form 1 | 1.0 mg |
| Colloidal silicon dioxide | 1.0 mg |
| Cellulose, microcryst | 56.0 mg |
| Modified cellulose gum | 2.0 mg |
| Magnesium stearate | Adequate amount |
| Coating | |
| HPMC | 3.0 mg |
| Mywacett 9~40 T approx. | 0.3 mg |

*Acylated monoglyceride used as plasticizer for film coating.

Example 28~Example 31

Tablet: ozanimod Form 1 of Example 27 was replaced by Form 2, Form 3, Form 4 and Form 5, respectively. The molar amount of the free base in the new formula was the same as that in ozanimod Form 1 of Example 27. Other components in the new formula and procedures of tableting were the same as those of Example 27.

Example 32

A typical capsule for oral administration contained ozanimod Form 1 (1.1 mg), lactose (75 mg) and magnesium stearate (2 mg). The mixture was passed through a 60 mesh sieve and packed into a No. 4 gelatin capsule.

Example 33~Example 36

Capsule: ozanimod Form 1 of Example 32 was replaced by Form 2, Form 3, Form 4 and Form 5, respectively. The molar amount of the free base in the new formula was the same as that in ozanimod Form 1 of Example 32. Other components in the new formula and procedures of capsulation were the same as those of Example 32.

Example 37

A typical injectable preparation was made by aseptically placing 1 mg ozanimod Form 1 into a vial, aseptically freeze-dried and sealed. For use, the contents of the vial were mixed with 2 mL of sterile physiological saline to produce an injectable preparation.

Example 38~Example 41

Injection: ozanimod Form 1 of Example 37 was replaced by Form 2, Form 3, Form 4 and Form 5, respectively. The molar amount of free base in the new formula was the same as that in ozanimod Form 1 of Example 37. Other components in the new formula and procedures of injection preparation were the same as those of Example 37.

Comparative Example 1

The known ozanimod solid of Preparation Example 1 and ozanimod Form 1 of Example 1 were tested in form stability test. The procedures are detailed as follows: placed about 20 mg of the above two samples respectively at 50° C., and studied their form stability.

TABLE 1

Experimental Data of Comparative Example 1

| Samples | Storage time | |
|---|---|---|
| | 0 day | 5 days |
| Ozanimod Form 1 of the present invention | Form 1 | Remained Form 1 |
| The known ozanimod | Amorphous | Weak diffraction peak appeared |

According to table 1, compared with the known ozanimod in the prior art, ozanimod Form 1 of the present invention is more stable.

Comparative Example 2

The form stability in water of the known ozanimod of Preparation Example 1 and ozanimod Form 2 of Example 10 were compared. The procedures are detailed as follows: took about 20 mg of the above two samples respectively, stirred in water, and studied the form stability.

TABLE 2

Experimental Data of Comparative Example 2

| Samples | Stirred in water for 3 days |
|---|---|
| Ozanimod Form 2 of the present invention | Remained Form 2 |
| The known ozanimod | Transformed to Form 2 |

According to table 2, compared with the known ozanimod in the prior art, ozanimod Form 2 of the present invention remained unchanged after stirring in water for 3 days, showing that ozanimod Form 2 is more stable in water.

Comparative Example 3

The known ozanimod of Preparation Example 1 and ozanimod Form 3 of Example 19 were compared in their form stability under 97% relative humidity. The procedures are detailed as follows: placed about 20 mg of the above two samples respectively at 97% RH environment, and studied their crystalline form stability.

| Samples | Storage time | |
|---|---|---|
| | 0 day | 5 days |
| Ozanimod Form 3 of the present invention | Form 3 | Remained Form 3 |
| The known ozanimod | Amorphous | Weak diffraction peak appeared |

According to table 3, compared with the known ozanimod in the prior art, ozanimod Form 3 of the present invention remained unchanged after having been storage at 97% RH for 10 days, showing that ozanimod Form 3 is more stable.

All patents, patent application publications, patent applications and non-patent publications cited in this specification are incorporated into this application by reference in their entireties.

The described above are only specific embodiments for illustrating the present invention, but without limiting it to that. Any changes or alternations, without creative work, made by those skilled in the art within the technical scope disclosed by the present invention, should fall within the scope of the present invention. Therefore, the scope of protection of the present invention shall be subject to the scope of protection defined in the claims

The invention claimed is:

1. Ozanimod Form 1 having the chemical structure shown in formula (I) below,

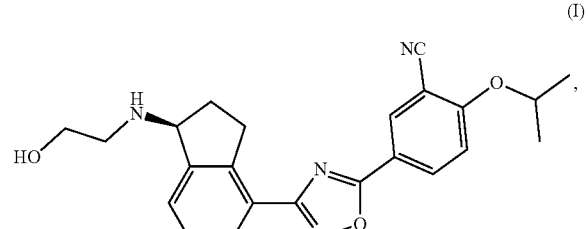

wherein the X-ray powder diffraction pattern of the ozanimod Form 1, expressed as 2θ angles, has the following characteristic peaks: 5.7±0.2°, 8.6±0.2°, 11.5±0.2°, 13.3±0.2°, 13.9±0.2°, 14.5±0.2°, 16.2±0.2°, 19.5±0.2°, 24.6±0.2°, 25.3±0.2°, 26.1±0.2° and 26.9±0.2°.

2. The ozanimod Form 1 according to claim 1, wherein the X-ray powder diffraction pattern of the ozanimod Form 1, expressed as 2θ angles, has the following characteristic peaks with their relative intensities:

| Diffraction angle 2θ | Relative intensity % |
|---|---|
| 5.7 ± 0.2° | 100.0 |
| 8.6 ± 0.2° | 27.6 |
| 11.5 ± 0.2° | 19.2 |
| 13.3 ± 0.2° | 41.3 |
| 13.9 ± 0.2° | 12.0 |
| 14.5 ± 0.2° | 10.7 |
| 16.2 ± 0.2° | 26.2 |
| 17.4 ± 0.2° | 10.5 |
| 19.5 ± 0.2° | 17.7 |
| 23.3 ± 0.2° | 11.1 |
| 24.6 ± 0.2° | 19.2 |
| 25.3 ± 0.2° | 18.7 |
| 26.1 ± 0.2° | 13.4 |
| 26.9 ± 0.2° | 16.2 |
| 27.9 ± 0.2° | 10.5 |
| 31.7 ± 0.2° | 12.8. |

3. The ozanimod Form 1 according to claim 1, wherein the Fourier transform infrared spectrum of the ozanimod Form 1 has characteristic peaks at wave numbers of 1485, 1461, 1370, 1349, 1287, 1104, 1066, 943, 831 and 758 cm$^{-1}$.

4. A pharmaceutical composition comprising a therapeutically and/or preventively effective amount of the ozanimod Form 1 according to claim 1, and at least one pharmaceutically acceptable carrier or additive.

5. The pharmaceutical composition according to claim 4, wherein the pharmaceutical composition is selected from the group consisting of tablets, capsules, powders, granules, solutions and suspensions.

6. A method of preparing the ozanimod Form 1 according to claim 1, comprising any one of the following methods:

(1) forming a suspension of ozanimod in $C_4$ to $C_6$ ether, $C_1$ to $C_4$ alcohol, cyclic ether, nitrile, water, alkane, nitromethane, or any mixture thereof, stirring for crystallization, then separating and drying to obtain the ozanimod Form 1; the stirring time is from 1 to 2 days; wherein:
the solvent is selected from the group consisting of diethyl ether, ethanol, acetonitrile, water, methanol, dichloromethane, nitromethane, heptane, and any mixture thereof;
the operation temperature of the preparation method is from 10° C. to 40° C.;
the drying temperature is from 10° C. to 60° C.;
the drying time is from 10 to 48 hours;
the weight to volume ratio of ozanimod to the solvent is from 5 mg: 1mL to 100 mg: 1 mL;

(2) forming a solution of ozanimod in a mixed solvent of nitromethane and alkane, $C_1$ to $C_4$ alcohol and alkane, or cyclic ether and water, then evaporating to obtain the ozanimod Form 1; wherein:
the mixed solvent is selected from the group consisting of nitromethane and heptane mixture, acetonitrile and water mixture, and dichloromethane and methanol mixture;
the evaporation temperature is from 10° C. to 60° C.;
the concentration of the solution of ozanimod is 0.5 to 1.0 times of the solubility of ozanimod in the selected solvent;

(3) heating a solution of ozanimod in nitromethane, haloalkane, cyclic ether, acetonitrile, or any mixture thereof to clear, stirring at low temperature for crystallization, then separating and drying to obtain the ozanimod Form 1; wherein:
the solvent is selected from the group consisting of nitromethane, acetonitrile, chloroform, and any mixture thereof;
the operation temperature of the preparation method is from 40° C. to 70° C.;
the low temperature is from -10° C. to 30° C.;
the drying temperature is from 10° C. to 40° C.;
the drying time is from 10 to 48 hours;
the weight to volume ratio of ozanimod to the solvent is from 5 mg:1 mL to 15 mg: 1 mL.

7. A method of modulation, activation, or stimulation of a sphingosine-1-phosphate (S1P) receptor, comprising contacting the S1P receptor with a therapeutically effective amount of the ozanimod Form 1 according to claim 1.

8. A method of treating multiple sclerosis, transplant rejection or acute respiratory distress syndrome in a subject in need of treatment, comprising administering to the subject a therapeutically effective amount of a pharmaceutical composition of the ozanimod Form 1 according to claim 1.

9. The method according to claim 8, wherein the treatment is for multiple sclerosis.

10. The method according to claim 8, wherein the treatment is for transplant rejection.

11. The method according to claim 8, wherein the treatment is for acute respiratory distress syndrome.

12. The method according to claim 8, wherein the pharmaceutical composition is a capsule.

13. The method according to claim 8, wherein the pharmaceutical composition is a tablet.

14. The method according to claim 8, wherein the therapeutically effective amount of the ozanimod Form 1 is about 1.0 mg.

15. The method according to claim 8, wherein the subject is a mammal.

16. The method according to claim 15, wherein the mammal is a human.

17. A method of treating multiple sclerosis, comprising administering to a human patient in need of treatment, an oral capsule comprising the ozanimod Form 1 according to claim 1, wherein the amount of ozanimod Form 1 in the capsule is about 1.0 mg.

* * * * *